(12) United States Patent
Kashiki

(10) Patent No.: US 11,547,639 B2
(45) Date of Patent: Jan. 10, 2023

(54) DENTAL COMPOSITION CONTAINING PLATINUM NANOPARTICLES

(71) Applicant: KURARAY NORITAKE DENTAL INC., Kurashiki (JP)

(72) Inventor: Nobusuke Kashiki, Aichi (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 0 days.

(21) Appl. No.: 16/772,604

(22) PCT Filed: Dec. 12, 2018

(86) PCT No.: PCT/JP2018/045727
§ 371 (c)(1),
(2) Date: Jun. 12, 2020

(87) PCT Pub. No.: WO2019/117206
PCT Pub. Date: Jun. 20, 2019

(65) Prior Publication Data
US 2020/0390661 A1  Dec. 17, 2020

(30) Foreign Application Priority Data

Dec. 13, 2017  (JP) .............................. JP2017-238324

(51) Int. Cl.
| A61K 6/844 | (2020.01) |
| A61K 6/889 | (2020.01) |
| A61K 33/24 | (2019.01) |
| A61K 33/244 | (2019.01) |
| A61K 33/243 | (2019.01) |

(52) U.S. Cl.
CPC .............. *A61K 6/844* (2020.01); *A61K 6/889* (2020.01); *A61K 33/24* (2013.01); *A61K 33/243* (2019.01); *A61K 33/244* (2019.01)

(58) Field of Classification Search
CPC .................................................... A61K 6/844
See application file for complete search history.

(56) References Cited

U.S. PATENT DOCUMENTS

| 4,719,297 A | 1/1988 | Henne et al. | |
| 8,436,070 B2 * | 5/2013 | Rheinberger | ................ 433/172 |

| 2003/0064102 A1 | 4/2003 | Nakatsuka | |
| 2007/0213460 A1 | 9/2007 | Ruppert et al. | |
| 2008/0248086 A1 * | 10/2008 | Asgari | .................... A61L 27/58 424/426 |
| 2014/0228473 A1 | 8/2014 | Osswald et al. | |

FOREIGN PATENT DOCUMENTS

| EP | 0 009 348 B1 | 7/1983 |
| JP | 57-197289 A | 12/1982 |
| JP | 5-32516 A | 2/1993 |
| JP | 9-3109 A | 1/1997 |
| JP | 10-245525 A | 9/1998 |
| JP | 2000-159621 A | 6/2000 |
| JP | 2002-47118 A | 2/2002 |
| JP | 2002-060805 | 2/2002 |
| JP | 2003-96122 A | 4/2003 |
| JP | 2007-514675 A | 6/2007 |
| JP | 2009-234932 A | 10/2009 |
| JP | 2014-129217 A | 7/2014 |
| JP | 2016-202864 A | 12/2016 |
| WO | WO 2009/125847 A1 | 10/2009 |
| WO | WO 2016/130985 A1 | 8/2016 |

OTHER PUBLICATIONS

Mafune et al (J. Phys. Chem. B 2003, 107, 4218-4223). (Year: 2003).*
International Search Report dated Jan. 22, 2019 in PCT/JP2018/045727 filed on Dec. 12, 2018, 2 pages.
Ma, S. et al., "Assessment of bactericidal effects of quaternary ammonium-based antibacterial monomers in combination with colloidal platinum nanoparticles," Dental Materials Journal, vol. 31, No. 1, 2012, pp. 150-156.
Hashimoto, M. et al., "Inhibitory Effect of Platinum Nanoparticles on Biofilm Formation of Oral Bacteria," Nano Biomedicine, vol. 9, No. 2, 2017, pp. 77-82.
Extended European Search Report dated Jul. 15, 2021 in European Patent Application No. 18889258.2, 11 pages.

* cited by examiner

*Primary Examiner* — Benjamin J Packard
(74) *Attorney, Agent, or Firm* — Oblon, McClelland, Maier & Neustadt, L.L.P.

(57) ABSTRACT

The present invention provides a dental composition that exhibits excellent long-lasting antibacterial activity even as a cured product, and that excels in aesthetic quality with no discoloration occurring in water or in hydrogen sulfide. The present invention relates to a dental composition comprising a platinum nanoparticle (a) uncoated with a colloidal protective material.

19 Claims, No Drawings

DENTAL COMPOSITION CONTAINING PLATINUM NANOPARTICLES

TECHNICAL FIELD

The present invention relates to an antibacterial dental composition comprising platinum nanoparticles. Specifically, the present invention relates to an antibacterial dental composition that comprises platinum nanoparticles uncoated with a protective material such as polyacrylic acid, and that is for use in the treatment of a decayed tooth. Particularly, the present invention relates to a dental bonding agent, a dental cement, and a dental composite resin that kill or inhibit growth of caries-causing bacteria present on teeth, among others.

BACKGROUND ART

In dental treatment, acrylic bonding agents or cements are often used for restoration of a lost tooth with a restoration material such as a dental composite resin, a dental metal alloy, porcelain, and zirconia. However, bacteria can still find a way through the interface between a tooth and a dental bonding agent or dental cement, and cause conditions such as secondary caries and pulpitis, necessitating another treatment. In order to prevent such entry of bacteria, Patent Literatures 1 and 2 attempt to mix an antibacterial compound into a dental bonding agent or dental cement.

Patent Literature 1 discloses a technique in which a polymerizable group-containing antibacterial salt compound is mixed into a composition containing an acidic group-containing polymerizable monomer, a hydrophilic polymerizable monomer, water, and a basic compound to enable inactivation of caries-causing bacteria remaining on teeth while maintaining desirable adhesiveness. Patent Literature 2 discloses a polymerizable dental material containing silver particles.

CITATION LIST

Patent Literature

Patent Literature 1: JP 2002-047118 A
Patent Literature 2: JP 2007-514675 A

SUMMARY OF INVENTION

Technical Problem

Studies by the present inventor revealed that the antibacterial composition of Patent Literature 1 has low antibacterial activity after polymerization and curing, and lacks long-lasting antibacterial activity as a cured product, though the composition itself was found to possess antibacterial activity. The dental material of Patent Literature 2 was also found to have antibacterial activity. However, the dental material of this related art, as a cured product after polymerization and curing, shows serious discoloration in water or in hydrogen sulfide produced in the oral cavity, and is not applicable to aesthetic restorative treatment.

It is accordingly an object of the present invention to provide a dental composition that exhibits excellent long-lasting antibacterial activity even as a cured product, and that excels in aesthetic quality with no discoloration occurring in water or in hydrogen sulfide.

Solution to Problem

The present inventor conducted intensive follow-up studies to find a solution to the foregoing problems, and found that the foregoing issues can be solved with a dental composition comprising a platinum nanoparticle (a) uncoated with a colloidal protective material. The present invention was completed on the basis of this finding.

The present invention includes the following.
[1] A dental composition comprising a platinum nanoparticle (a) uncoated with a colloidal protective material.
[2] The dental composition according to [1], comprising a complex (c) in which the platinum nanoparticle (a) is supported on a surface of a core particle (b).
[3] The dental composition according to [2], wherein the core particle (b) is at least one kind of particle selected from the group consisting of a ceramic, catechin, a vitamin derivative, astaxanthin, a placenta extract, a coenzyme, and hyaluronan.
[4] The dental composition according to any one of [1] to [3], wherein the dental composition further comprises a radical polymerizable monomer (d) and a polymerization initiator (e).
[5] The dental composition according to [4], wherein the radical polymerizable monomer (d) is a (meth)acrylate polymerizable monomer (d1) and/or a (meth)acrylamide polymerizable monomer (d2).
[6] The dental composition according to [5], wherein the (meth)acrylate polymerizable monomer (d1) comprises an aromatic bifunctional (meth)acrylate polymerizable monomer and/or an aliphatic bifunctional (meth)acrylate polymerizable monomer.
[7] The dental composition according to any one of [1] to [6], wherein the platinum nanoparticle (a) is contained in an amount of 0.005 to 5.0 ppm by mass.
[8] The dental composition according to any one of [1] to [7], wherein the dental composition further comprises a filler (f).

Advantageous Effects of Invention

A dental composition of the present invention can prevent penetration of bacteria into a tooth because of the excellent long-lasting antibacterial activity exhibited by the dental composition even as a cured product, and excels in aesthetic quality with reduced discoloration occurring in water and in hydrogen sulfide. This makes a dental composition of the present invention best suited for aesthetic restorative treatment. A dental composition of the present invention can reduce discoloration that occurs in water and in hydrogen sulfide under high temperature conditions. This means that discoloration after an aesthetic restorative treatment can be reduced even with a relatively high temperature material (for example, a drink) being present in the oral cavity.

DESCRIPTION OF EMBODIMENTS

A dental composition of the present invention comprises a platinum nanoparticle (a) uncoated with a colloidal protective material (hereinafter, also referred to simply as "platinum nanoparticle (a)").

Platinum Nanoparticle (a)

The following describes the platinum nanoparticle (a) contained in a dental composition of the present invention.

The platinum forming the platinum nanoparticle (a) comprises primarily elemental platinum metal particles. The content of the elemental platinum metal particles in the platinum nanoparticle (a) is preferably 50 mass % or more, more preferably 70 mass % or more, even more preferably 90 mass % or more, particularly preferably 99 mass % or more.

It is required in the present invention that the platinum nanoparticle (a) be uncoated with a colloidal protective material. It appears that the platinum nanoparticles, with no colloidal protective material coating, become negatively charged after repeated contact with water molecules, and develop a long-lasting, desirable antibacterial activity even in the form of a cured product. The type of colloidal protective material is not limited. The platinum nanoparticle (a) may or may not be forming a colloid.

The platinum nanoparticle (a) has an average particle diameter in a range of preferably 1 to 50 nm, more preferably 1 to 5 nm. With the average particle diameter confined in these ranges, the platinum nanoparticle (a) is able to sufficiently develop its antibacterial effect in the form of a cured product while reducing discoloration in water and in hydrogen sulfide. The average particle diameter of platinum nanoparticle (a) can be determined by electron microscopy. Specifically, particles may be photographed with a scanning electron microscope (Model S-4000, manufactured by Hitachi), and the size of particles (at least 200 particles) observed in a unit field of the micrograph may be measured using image-analyzing particle-size-distribution measurement software (Macview; Mountech Co., Ltd.). Here, the particle diameter is determined as an arithmetic mean value of the maximum and minimum lengths of particles, and the average primary particle diameter is calculated from the number of particles and the particle diameter.

The platinum nanoparticle (a) is produced as follows. First, a platinum plate as a nanoparticle source is immersed in a solvent (for example, water), and a laser beam and ultrasonic waves are simultaneously applied to the target platinum plate from a laser beam source and an ultrasonic vibrator, respectively. By being bombarded with a laser beam in water, the platinum plate can form fine nanoparticles while the ultrasonic waves inhibit aggregation of the generated platinum nanoparticles. The laser beam and ultrasonic application can also result in producing an aqueous dispersion or suspension of platinum nanoparticles uncoated with an organic protective material such as a polymerization agent (platinum nanoparticle-dispersed aqueous solution). The metal nanoparticle formation using a laser in water is based on the principle of liquid-phase laser abrasion. Aggregation of platinum nanoparticle (a) can be inhibited by storing the platinum nanoparticles in the form of a platinum nanoparticle-dispersed aqueous solution.

The content of platinum nanoparticle (a) is preferably 0.005 to 5.0 ppm by mass relative to the mass of the dental composition. For improved antibacterial activity and reduced discoloration, the content of platinum nanoparticle (a) is more preferably 0.05 to 2.5 ppm by mass, even more preferably 0.15 to 1.5 ppm by mass. With a platinum nanoparticle (a) content of less than 0.005 ppm by mass, the dental composition produced may fail to show antibacterial activity. With a platinum nanoparticle (a) content of more than 5.0 ppm by mass, the dental composition and a cured product thereof may turn black in color. The content of platinum nanoparticle (a) remains the same even when the platinum nanoparticle (a) is forming a complex (c), as will be described later.

The dental composition of the present invention may comprise the platinum nanoparticle (a) in the form of a dispersion of solely platinum nanoparticle (a). In another embodiment, the dental composition of the present invention may comprise a complex (c) in which the platinum nanoparticle (a) is supported on a surface of a core particle (b). Such a dental composition with complex (c) is also able to show a long-lasting, desirable antibacterial activity while reducing discoloration in water and in hydrogen sulfide, even in the form of a cured product. The complex (c) is produced as follows, for example.

A core particle (b) having a larger average particle diameter than the platinum nanoparticle (a) is mixed into a platinum nanoparticle-dispersed aqueous solution containing platinum nanoparticle (a) to make the platinum nanoparticle (a) adhere to the surface of the core particle (b). Because the platinum nanoparticle (a) dispersed in water is active, the platinum nanoparticle (a) is able to adhere to the large surface of core particle (b) upon introduction of the core particle (b). After producing dried particles by a method such as spray drying, the particles are heated at 900° C. for about 1 hour in a hydrogen atmosphere to remove moisture and obtain a complex (c) in which the platinum nanoparticle (a) is supported on the surface of the core particle (b).

Examples of the core particle (b) include a ceramic particle (such as silica, alumina, titanium oxide, zirconia, and silicon carbide), catechin, vitamin derivatives, astaxanthin, a placenta extract, coenzymes, and hyaluronan. Preferably, the core particle (b) is at least one kind of particle selected from the group consisting of these, and the core particle (b) may be used alone, or two or more thereof may be used in combination. For handling, the core particle (b) has an average particle diameter of preferably 0.01 to 10 μm, though the average particle diameter of core particle (b) is not limited, as long as it is larger than the particle diameter of platinum nanoparticle (a). The average particle diameter of core particle (b) can be measured by electron microscopy, as with the case of platinum nanoparticle (a).

In a certain embodiment using complex (c), it is required that the platinum nanoparticle (a) be supported on the surface of the core particle (b) in the complex (c). However, particles (for example, silver) other than platinum nanoparticle (a) may be supported, as long as the present invention can exhibit its effects. The complex (c) has an average particle diameter in a range of preferably 5 to 2,000 nm, more preferably 50 to 1,000 nm. With the average particle diameter of complex (c) confined in these ranges, the platinum nanoparticle (a) is able to sufficiently develop its antibacterial effect in the form of a cured product. The average particle diameter of complex (c) can be measured in the same way as for the platinum nanoparticle (a). A laser diffraction scattering method can be conveniently used for the measurement of particles larger than 100 nm. Specifically, the average particle diameter of complex (c) can be measured with, for example, a laser diffraction particle size distribution analyzer (SALD-2300, Shimadzu Corporation), using a 0.2% sodium hexametaphosphate aqueous solution as dispersion medium.

Preferably, the dental composition of the present invention further comprises a radical polymerizable monomer (d) and a polymerization initiator (e). For example, a dental composition of the present invention containing a radical polymerizable monomer (d) and a polymerization initiator (e) can be used to prepare dental materials such as dental bonding agents, dental cements, and dental composite resins.

Radical Polymerizable Monomer (d)

The radical polymerizable monomer (d) used in the present invention is not particularly limited, as long as it is a radical polymerizable monomer having a polymerizable group. Preferred examples of such compounds include compounds having an acryloyl group or a methacryloyl group, specifically, a (meth)acrylate polymerizable monomer (d1) and a (meth)acrylamide polymerizable monomer (d2). As used herein, "(meth)acryl" is a collective term for methacryl and acryl. The radical polymerizable monomer (d) may be used alone, or two or more thereof may be used in combination. In a certain preferred embodiment, the dental composition comprises a (meth)acrylate polymerizable monomer (d1) and/or a (meth)acrylamide polymerizable monomer (d2).

Examples of the (meth)acrylate polymerizable monomer (d) include:

aliphatic monofunctional (meth)acrylate polymerizable monomers such as methyl(meth)acrylate, ethyl(meth)acrylate, propyl(meth)acrylate, butyl(meth)acrylate, isobutyl (meth)acrylate, lauryl(meth)acrylate, 2,3-dibromopropyl (meth)acrylate, methoxypolyethylene glycol(meth)acrylate, glycidyl(meth)acrylate, 2-hydroxyethyl(meth)acrylate, 3-hydroxypropyl(meth)acrylate, 3-chloro-2-hydroxypropyl (meth)acrylate, and tetrahydrofurfuryl(meth)acrylate;

aromatic monofunctional (meth)acrylate polymerizable monomers such as benzyl(meth)acrylate, phenoxyethyl (meth)acrylate, phenoxydiethylene glycol(meth)acrylate, phenoxypolyethylene glycol(meth)acrylate, 2-hydroxy-3-phenoxypropyl(meth)acrylate, 2-(meth)acryloyloxyethyl-2-hydroxyethyl-phthaic acid, and neopentyl glycol-(meth) acrylic acid-benzoic acid ester;

aliphatic bifunctional (meth)acrylate polymerizable monomers such as 1,2-bis(3-methacryloyloxy-2-hydroxypropoxy)ethane, ethylene glycol di(meth)acrylate, diethylene glycol di(meth)acrylate, triethylene glycol di(meth) acrylate, polyethylene glycol di(meth)acrylate, propylene glycol di(meth)acrylate, butylene glycol di(meth)acrylate, neopentyl glycol di(meth)acrylate, erythritol di(meth)acrylate, sorbitol di(meth)acrylate, mannitol di(meth)acrylate, pentaerythritol di(meth)acrylate, dipentaerythritol di(meth) acrylate, glycerol di(meth)acrylate, 1,3-butanediol di(meth) acrylate, 1,5-pentanediol di(meth)acrylate, 1,6-hexanediol di(meth)acrylate, 1,10-decanediol di(meth)acrylate, tricyclodecanedimethanol di(meth)acrylate, and 1,2-bis(3-methacryloyloxy-2-hydroxypropoxy)ethane;

aromatic bifunctional (meth)acrylate polymerizable monomers such as 2,2-bis[4-(3-(meth)acryloyloxy-2-hydroxypropoxy)phenyl]propane, 2,2-bis[4-(4-(meth)acryloyloxy)-3-hydroxybutoxyphenyl]propane, 2,2-bis[4-(4-(meth) acryloyloxy)-2-hydroxybutoxyphenyl]propane, 2,2-bis[4-(5-(meth)acryloyloxy)-4-hydroxypentoxyphenyl]propane, 2,2-bis((meth)acryloyloxyphenyl)propane, 2,2-bis(4-(meth) acryloyloxyethoxyphenyl)propane, 2,2-bis(4-(meth)acryloyloxydiethoxyphenyl)propane, 2,2-bis(4-(meth)acryloyloxytriethoxyphenyl)propane, 2,2-bis(4-(meth) acryloyloxytetraethoxyphenyl)propane, 2,2-bis(4-(meth) acryloyloxypentaethoxyphenyl)propane, 2-(4-(meth) acryloyloxydiethoxyphenyl)-2-(4-(meth) acryloyloxyethoxyphenyl)propane, 2-(4-(meth) acryloyloxydiethoxyphenyl)-2-(4-(meth) acryloyloxytriethoxyphenyl)propane, 2,2-bis(4-(meth) acryloyloxypolyethoxyphenyl)propane, 2-(4-(meth) acryloyloxydipropoxyphenyl)-2-(4-(meth) acryloyloxytriethoxyphenyl)propane, 2,2-bis(4-(meth) acryloyloxypropoxyphenyl)propane, 2,2-bis(4-(meth) acryloyloxydipropoxyphenyl)propane, and 2,2-bis(4-(meth) acryloyloxyisopropoxyphenyl)propane; and tri- and higher-functional (meth)acrylate polymerizable monomers such as trimethylolpropane tri(meth)acrylate, trimethylolethane tri(meth)acrylate, trimethylolmethane tri (meth)acrylate, pentaerythritol tri(meth)acrylate, pentaerythritol tetra(meth)acrylate, dipentaerythritol tri(meth) acrylate, dipentaerythritol tetra(meth)acrylate, dipentaerythritol penta(meth)acrylate, N,N-(2,2,4-trimethylhexamethylene)bis[2-(aminocarboxy)propane-1,3-diol]tetramethacrylate, 1,7-diacryloyloxy-2,2,6,6-tetraacryloyloxymethyl-4-oxyheptane, 1,7-diacryloyloxy-2,2,6,6-tetraacryloyloxymethyl-4-oxyheptane, and 1,7-di(meth) acryloyloxy-2,2,6,6-tetra(meth)acryloyloxymethyl-4-oxaheptane dipentaerythritol hexa(meth)acrylate.

In a certain preferred embodiment, the (meth)acrylate polymerizable monomer (d1) contained in the dental composition is an aromatic bifunctional (meth)acrylate polymerizable monomer and/or an aliphatic bifunctional (meth) acrylate polymerizable monomer.

Examples of the (meth)acrylamide polymerizable monomer (d2) include: monofunctional (meth)acrylamide polymerizable monomers such as N,N-diethyl(meth)acrylamide, N,N-dimethyl(meth)acrylamide, N-methylol(meth)acrylamide, N-(2-hydroxyethyl)(meth)acrylamide, N-(2,3-dihydroxypropyl)(meth)acrylamide, diacetone(meth)acrylamide, and 4-(meth)acryloylmorpholine;

bifunctional (meth)acrylamide polymerizable monomers such as N,N'-ethylenebis(meth)acrylamide, N,N'-propylenebis(meth)acrylamide, N,N'-butylenebis(meth)acrylamide, N,N'-(dimethyl)ethylenebis(meth)acrylamide, N,N'-diethyl-1,3-propylenebis(meth)acrylamide, bis[2-(2-methyl-(meth) acrylamino)ethoxycarbonyl]hexamethylenediamine, 2,2,4-trimethylhexamethylene-1,6-bis(meth)acrylamide, N-methacryloyloxyethylacrylamide, N-methacryloyloxypropylacrylamide, N-methacryloyloxybutylacrylamide, N-(1-ethyl-(2-methacryloyloxy)ethyl)acrylamide, and N-(2-(2-methacryloyloxyethoxy)ethyl)acrylamide; and tri- and higher-functional (meth)acrylamide polymerizable monomers such as N,N',N'',N'''-tetraacryloyltriethylenetetramine.

An acidic group-containing radical polymerizable monomer (d3) may be contained as a radical polymerizable monomer (d) to allow the dental composition to penetrate and bind to tooth structure through demineralization, and improve adhesiveness for tooth structure. The acidic group-containing radical polymerizable monomer (d3) is a polymerizable monomer having at least one acidic group such as a phosphoric acid group, a phosphonic acid group, a pyrophosphoric acid group, a carboxylic acid group, or a sulfonic acid group, and at least one radical polymerizable group such as an acryloyl group, a methacryloyl group, an acrylamide group, or a methacrylamide group. In view of adhesiveness for enamel, the acidic group-containing radical polymerizable monomer (d3) is preferably a monofunctional compound having at least one of an acryloyl group, a methacryloyl group, an acrylamide group, and a methacrylamide group. Specific examples include the following.

Examples of the phosphoric acid group-containing (meth) acrylic monomer include 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth) acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyicosyl dihydrogen phosphate, bis[2-(meth)acryloyloxyethyl]hydrogen phosphate, bis[4-(meth)acryloyloxybutyl]hydrogen phosphate, bis[6-(meth) acryloyloxyhexyl]hydrogen phosphate, bis[8-(meth)acryloyloxyoctyl]hydrogen phosphate, bis[9-(meth) acryloyloxynonyl]hydrogen phosphate, bis[10-(meth) acryloyloxydecyl]hydrogen phosphate, 1,3-di(meth) acryloyloxypropyl dihydrogen phosphate, 2-(meth)

acryloyloxyethylphenyl hydrogen phosphate, 2-(meth)acryloyloxyethyl-2-bromoethyl hydrogen phosphate, 2-(meth)acryloyloxyethyl-(4-methoxyphenyl)hydrogen phosphate, 2-(meth)acryloyloxypropyl-(4-methoxyphenyl) hydrogen phosphate, and acid chlorides, alkali metal salts, ammonium salts, and amine salts thereof.

Examples of the phosphonic acid group-containing (meth)acrylic monomer include 2-(meth)acryloyloxyethylphenylphosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexylphosphonoacetate, 10-(meth)acryloyloxydecylphosphonoacetate, and acid chlorides, alkali metal salts, ammonium salts, and amine salts thereof.

Examples of the pyrophosphoric acid group-containing (meth)acrylic monomer include bis[2-(meth)acryloyloxyethyl]pyrophosphate, bis[4-(meth)acryloyloxybutyl]pyrophosphate, bis[6-(meth)acryloyloxyhexyl]pyrophosphate, bis[8-(meth)acryloyloxyoctyl]pyrophosphate, bis[10-(meth)acryloyloxydecyl]pyrophosphate, and acid chlorides, alkali metal salts, ammonium salts, and amine salts thereof.

Examples of the carboxylic acid group-containing (meth)acrylic monomer include:

(meth)acrylic acid;
4-(meth)acryloyloxyethoxycarbonylphthalic acid;
4-(meth)acryloyloxyethyltrimellitic acid, 4-(meth)acryloyloxybutyloxycarbonylphthalic acid, 4-(meth)acryloyloxyhexyloxycarbonylphthalic acid, 4-(meth)acryloyloxyoctyloxycarbonylphthalic acid, 4-(meth)acryloyloxydecyloxycarbonylphthalic acid, and acid anhydrides thereof;
5-(meth)acryloylaminopentylcarboxylic acid;
6-(meth)acryloyloxy-1,1-hexane dicarboxylic acid;
8-(meth)acryloyloxy-1,1-octane dicarboxylic acid;
10-(meth)acryloyloxy-1,1-decane dicarboxylic acid;
11-(meth)acryloyloxy-1,1-undecane dicarboxylic acid, and
acid chlorides, alkali metal salts, ammonium salts, and amine salts thereof.

Examples of the sulfonic acid group-containing (meth)acrylic monomer include 2-(meth)acrylamide-2-methylpropanesulfonic acid, 2-sulfoethyl(meth)acrylate, and acid chlorides, alkali metal salts, ammonium salts, and amine salts thereof.

Preferred as the acidic group-containing radical polymerizable monomer (d3) are phosphoric acid group- or pyrophosphoric acid group-containing (meth)acrylic monomers, particularly phosphoric acid group-containing (meth)acrylic monomers, because these monomers exhibit more desirable bond strength for tooth structure. Divalent phosphoric acid group-containing (meth)acrylic monomers in which an alkyl or alkylene group having 6 to 20 carbon atoms is contained as a main chain within the molecule are more preferred, and divalent phosphoric acid group-containing (meth)acrylic monomers in which an alkylene group having 8 to 12 carbon atoms is contained as a main chain within the molecule (e.g., 10-methacryloyloxydecyl dihydrogen phosphate) are most preferred.

The acidic group-containing radical polymerizable monomer (d3) may be used alone, or two or more thereof may be used in combination. With an excessively low content of acidic group-containing radical polymerizable monomer (d3), it may not be possible to obtain the effect produced by containing the monomer (d3). With an excessively high content of acidic group-containing radical polymerizable monomer (d3), the radical polymerizable monomer (d) tends to more readily undergo polymerization in the dental composition, with the result that the storage stability of the dental composition may decrease. It is accordingly preferable that the acidic group-containing radical polymerizable monomer (d3) be contained in an amount of 0.5 to 20 parts by mass, more preferably 1 to 15 parts by mass, even more preferably 2 to 10 parts by mass in 100 parts by mass of the radical polymerizable monomers contained in the dental composition.

Polymerization Initiator (e)

The polymerization initiator (e) used in the present invention may be a known polymerization initiator. Specifically, it is preferable to use a photopolymerization initiator and a chemical polymerization initiator. Individually, the photopolymerization initiator and the chemical polymerization initiator may be used alone, or two or more thereof may be used in appropriate combination.

Examples of the photopolymerization initiator include (bis)acylphosphine oxides, water-soluble acylphosphine oxides, thioxanthones or quaternary ammonium salts thereof, ketals, α-diketones, coumarins, anthraquinones, benzoinalkyl ethers, and α-aminoketones.

Examples of the acylphosphine oxides in the (bis)acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, benzoyl di(2,6-dimethylphenyl)phosphonate, and salts thereof (such as sodium salts, potassium salts, and ammonium salts). Examples of the bisacylphosphine oxides include bis(2,6-dichlorobenzoyl)phenylphosphine oxide, bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl)phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, bis(2,4,6-trimethylbenzoyl)phenylphosphine oxide, bis(2,5,6-trimethylbenzoyl)-2,4,4-trimethylpentylphosphine oxide, and salts thereof (such as sodium salts, potassium salts, and ammonium salts).

Preferably, the water-soluble acylphosphine oxides contain alkali metal ions, alkali earth metal ions, pyridinium ions, or ammonium ions within the acylphosphine oxide molecule. For example, the water-soluble acylphosphine oxides may be synthesized using the methods disclosed in European Patent No. 0009348 or JP 57(1982)-197289 A.

Specific examples of the water-soluble acylphosphine oxides include sodium monomethylacetylphosphonate, sodium monomethyl(1-oxopropyl)phosphonate, sodium monomethylbenzoylphosphonate, sodium monomethyl(1-oxobutyl)phosphonate, sodium monomethyl(2-methyl-1-oxopropyl)phosphonate, sodium acetylphosphonate, sodium acetylmethylphosphonate, sodium methyl 4-(hydroxymethoxyphosphinyl)-4-oxobutanoate, monosodium methyl 4-oxo-phosphonobutanoate, sodium acetylphenylphosphinate, sodium (1-oxopropyl)pentylphosphinate, sodium methyl 4-(hydroxypentylphosphinyl)-4-oxobutanoate, sodium acetylpentylphosphinate, sodium acetylethylphosphinate, sodium methyl(1,1-dimethyl)methylphosphinate, sodium (1,1-dimethoxyethyl)methylphosphinate, sodium (1,1-diethoxyethyl)methylphosphinate, lithium methyl 4-(hydroxymethylphosphinyl)-4-oxobutanoate, dilithium 4-(hydroxymethylphosphinyl)-4-oxobutanoate, sodium methyl(2-methyl-1,3-dioxolan-2-yl)phosphinate, sodium methyl(2-methyl-1,3-thiazolidin-2-yl)phosphonite, sodium (2-methylperhydro-1,3-diazin-2-yl)phosphonite, sodium acetylphosphinate, sodium (1,1-diethoxyethyl)phosphonite, sodium (1,1-diethoxyethyl)methylphosphonite, sodium methyl(2-methyloxathiolan-2-yl)phosphinate, sodium methyl(2,4,5-trimethyl-1,3-dioxolan-2-yl)phosphinate, sodium methyl(1,1-dipropoxyethyl)phosphinate, sodium (1-methoxyvinyl)methylphosphinate, sodium (1-ethylthiovinyl)methylphosphinate, sodium methyl(2-methylperhydro-1,3-diazin-2-yl)phosphinate, sodium methyl(2-methylperhydro-1,3-thiazin-2-yl)phosphinate, sodium methyl(2-methyl-1,3-diazolidin-2-yl)phosphinate, sodium methyl(2-methyl-1,3-thiazolidin-2-yl)phosphinate, sodium (2,2-dicyano-1-methylethynyl)phosphinate, sodium acetylmethylphosphinateoxime, sodium acetylmethylphosphinate-O-benzyloxime, sodium 1-[(N-ethoxyimino)ethyl]methylphosphinate, sodium methyl(1-phenyliminoethyl)phosphinate, sodium methyl(1-phenylhydrazoneethyl)phosphinate, sodium [1-(2,4-dinitrophenylhydrazono)ethyl]methylphosphinate, sodium acetylmethylphosphinate semicarbazone, sodium (1-cyano-1-hydroxyethyDmethylphosphinate, sodium (dimethoxymethyl)methylphosphinate, sodium formylmethylphosphinate, sodium (1,1-dimethoxypropyl)methylphosphinate, sodium methyl(1-oxopropyl)phosphinate, dodecylguanidine (1,1-dimethoxypropyl)methylphosphinate, isopropylamine (1,1-dimethoxypropyl)methylphosphinate, sodium acetylmethylphosphinate thiosemicarbazone, 1,3,5-tributyl-4-methylamino-1,2,4-triazolium (1,1-dimethoxyethyl)methylphosphinate, 1-butyl-4-butylaminomethylamino-3,5-dipropyl-1,2,4-triazolium (1,1-dimethoxyethyl) ethylphosphinate, sodium salts of 2,4,6-trimethylbenzoylphenylphosphine oxide, potassium salts of 2,4,6-trimethylbenzoylphenylphosphine oxide, and ammonium salts of 2,4,6-trimethylbenzoylphenylphosphine oxide. Other examples include the compounds mentioned in JP 2000-159621 A.

Particularly preferred among these (bis)acylphosphine oxides and water-soluble acylphosphine oxides are 2,4,6-trimethylbenzoyldiphenylphosphine oxide, 2,4,6-trimethylbenzoylmethoxyphenylphosphine oxide, bis(2,4,6-trimethylbenzoyl)phenylphosphine oxide, and sodium salts of 2,4,6-trimethylbenzoylphenylphosphine oxide.

Examples of the thioxanthones or quaternary ammonium salts thereof include thioxanthone, 2-chlorothioxanthen-9-one, 2-hydroxy-3-(9-oxo-9H-thioxanthen-4-yloxy)-N,N,N-trimethyl-1-propaneaminium chloride, 2-hydroxy-3-(1-methyl-9-oxo-9H-thioxanthen-4-yloxy)-N,N,N-trimethyl-1-propanea minium chloride, 2-hydroxy-3-(9-oxo-9H-thioxanthen-2-yloxy)-N,N,N-trimethyl-1-propaneaminium chloride, 2-hydroxy-3-(3,4-dimethyl-9-oxo-9H-thioxanthen-2-yloxy)-N,N,N-trimethyl-1-propaneaminium chloride, 2-hydroxy-3-(3,4-dimethyl-9H-thioxanthen-2-yloxy)-N,N,N-trimethyl-1-propaneaminium chloride, and 2-hydroxy-3-(1,3,4-trimethyl-9-oxo-9H-thioxanthen-2-yloxy)-N,N,N-trimethyl-1-propaneaminium chloride.

Among these thioxanthones and quaternary ammonium salts thereof, 2-chlorothioxanthen-9-one is particularly preferred as a thioxanthone, and 2-hydroxy-3-(3,4-dimethyl-9H-thioxanthen-2-yloxy)-N,N,N-trimethyl-1-propaneaminium chloride is particularly preferred as a quaternary ammonium salt of thioxanthones.

Examples of the ketals include benzyl dimethyl ketal, and benzyl diethyl ketal.

Examples of the α-diketones include diacetyl, benzyl, dl-camphorquinone, 2,3-pentadione, 2,3-octadione, 9,10-phenanthrenequinone, 4,4'-oxybenzyl, and acenaphthenequinone. Particularly preferred is dl-camphorquinone for its maximum absorption wavelength occurring in the visible light region.

Examples of the coumarins include the compounds mentioned in JP 9(1997)-3109 A and JP 10(1998)-245525 A, including 3,3'-carbonylbis(7-diethylaminocoumarin), 3-(4-methoxybenzoyl)coumarin, 3-thienoylcoumarin, 3-benzoyl-5,7-dimethoxycoumarin, 3-benzoyl-7-methoxycoumarin, 3-benzoyl-6-methoxycoumarin, 3-benzoyl-8-methoxycoumarin, 3-benzoylcoumarin, 7-methoxy-3-(p-nitrobenzoyl) coumarin, 3-(p-nitrobenzoyl)coumarin, 3,5-carbonylbis(7-methoxycoumarin), 3-benzoyl-6-bromocoumarin, 3,3'-carbonylbiscoumarin, 3-benzoyl-7-dimethylaminocoumarin, 3-benzoylbenzo[f]coumarin, 3-carboxycoumarin, 3-carboxy-7-methoxycoumarin, 3-ethoxycarbonyl-6-methoxycoumarin, 3-ethoxycarbonyl-8-methoxycoumarin, 3-acetylbenzo[f]coumarin, 3-benzoyl-6-nitrocoumarin, 3-benzoyl-7-diethylaminocoumarin, 7-dimethylamino-3-(4-methoxybenzoyl)coumarin, 7-diethylamino-3-(4-methoxybenzoyl)coumarin, 7-diethylamino-3-(4-diethylamino)coumarin, 7-methoxy-3-(4-methoxybenzoyl)coumarin, 3-(4-nitrobenzoyl)benzo[f]coumarin, 3-(4-ethoxycinnamoyl)-7-methoxycoumarin, 3-(4-dimethylaminocinnamoyl)coumarin, 3-(4-diphenylaminocinnamoyl)coumarin, 3-[(3-dimethylbenzothiazol-2-ylidene)acetyl]coumarin, 3-[(1-methylnaphtho[1,2-d]thiazol-2-ylidene)acetyl]coumarin, 3,3'-carbonylbis(6-methoxycoumarin), 3,3'-carbonylbis(7-acetoxycoumarin), 3,3'-carbonylbis(7-dimethylaminocoumarin), 3-(2-benzothiazoyl)-7-(diethylamino)coumarin, 3-(2-benzothiazoyl)-7-(dibutylamino)coumarin, 3-(2-benzoimidazoyl)-7-(diethylamino)coumarin, 3-(2-benzothiazoyl)-7-(dioctylamino)coumarin, 3-acetyl-7-(dimethylamino)coumarin, 3,3'-carbonylbis(7-dibutylaminocoumarin), 3,3'-carbonyl-7-diethylaminocoumarin-7'-bis(butoxyethyl)aminocoumarin, 10-[3-[4-(dimethylamino)phenyl]-1-oxo-2-propenyl]-2,3,6,7-tetrahydro-1,1,7,7-tetram ethyl 1H,5H,11H-[1]benzopyrrano[6,7,8-ij]quinolizin-11-one, and 10-(2-benzothiazoyl)-2,3,6,7-tetrahydro-1,1,7,7-tetramethyl 1H,5H,11H-[1] benzopyrrano[6,7,8-ij]quinolizin-11-one.

Particularly preferred among these coumarins are 3,3'-carbonylbis(7-diethylaminocoumarin) and 3,3'-carbonylbis(7-dibutylaminocoumarin).

Examples of the anthraquinones include anthraquinone, 1-chloroanthraquinone, 2-chloroanthraquinone, 1-bromoanthraquinone, 1,2-benzanthraquinone, 1-methylanthraquinone, 2-ethylanthraquinone, and 1-hydroxyanthraquinone.

Examples of the benzoin alkyl ethers include benzoin methyl ether, benzoin ethyl ether, benzoin isopropyl ether, and benzoin isobutyl ether.

Examples of the α-aminoketones include 2-methyl-1-[4-(methylthio)phenyl]-2-morpholinopropan-1-one.

Among the photopolymerization initiators listed above, it is preferable to use at least one selected from the group consisting of a (bis)acylphosphine oxide, an α-diketone, and a coumarin. In this way, a dental composition can be provided that has desirable photocurability both in the visible light region and the near ultraviolet region so that sufficient photocurability can be ensured regardless of whether the light source used is a halogen lamp, a light emitting diode (LED), or a xenon lamp.

The chemical polymerization initiator as a polymerization initiator (e) used in the present invention is preferably an organic peroxide. The organic peroxide used as the chemical polymerization initiator is not particularly limited, and may be a known organic peroxide. Typical examples of such organic peroxides include ketone peroxides, hydroperoxides, diacyl peroxides, dialkyl peroxides, peroxy ketals, peroxy esters, and peroxy dicarbonates.

Examples of the ketone peroxides include methyl ethyl ketone peroxide, methyl isobutyl ketone peroxide, methylcyclohexanone peroxide, and cyclohexanone peroxide.

Examples of the hydroperoxides include 2,5-dimethylhexane-2,5-dihydroperoxide, diisopropylbenzenehydroperoxide, cumenehydroperoxide, t-butylhydroperoxide, and 1,1,3,3-tetramethylbutylhydroperoxide.

Examples of the diacyl peroxides include acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide.

Examples of the dialkyl peroxides include di-t-butyl peroxide, dicumyl peroxide, t-butylcumyl peroxide, 2,5-dimethyl-2,5-di(t-butylperoxy)hexane, 1,3-bis(t-butylperoxyisopropyl)benzene, and 2,5-dimethyl-2,5-di(t-butylperoxy)-3-hexyne.

Examples of the peroxy ketals include 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane, and n-butyl 4,4-bis(t-butylperoxy)valerate.

Examples of the peroxy esters include α-cumyl peroxyneodecanoate, t-butyl peroxyneodecanoate, t-butyl peroxypivalate, 2,2,4-trimethylpentylperoxy-2-ethylhexanoate, t-amyl peroxy-2-ethylhexanoate, t-butyl peroxy-2-ethylhexanoate, di-t-butyl peroxyisophthalate, di-t-butyl peroxyhexahydroterephthalate, t-butyl peroxy-3,3,5-trimethylhexanoate, t-butyl peroxyacetate, t-butyl peroxybenzoate, and t-butyl peroxymaleate.

Examples of the peroxy dicarbonates include di-3-methoxyperoxy dicarbonate, di-2-ethylhexylperoxy dicarbonate, bis(4-t-butylcyclohexyl)peroxy dicarbonate, diisopropylperoxy dicarbonate, di-n-propylperoxy dicarbonate, di-2-ethoxyethylperoxy dicarbonate, and diallylperoxy dicarbonate.

In a dental composition of the present invention, the polymerization initiator (e) may be used alone, or two or more thereof may be used in combination. The content of the polymerization initiator (e) used in the present invention is not particularly limited. However, in view of the curability and other properties of the dental composition produced, the content of polymerization initiator (e) ranges preferably from 0.005 to 10 parts by mass, more preferably 0.02 to 5 parts by mass relative to total 100 parts by mass of the radical polymerizable monomer(s) (d). With a polymerization initiator (e) content of more than 10 parts by mass, it may not be possible to obtain a sufficient bond strength when the polymerization initiator (e) itself is not highly polymerizable.

In a dental composition of the present invention, the polymerization initiator (e) is used preferably with a polymerization accelerator (g). Examples of the polymerization accelerator (g) include amines, sulfinic acid and salts thereof, borate compounds, derivatives of barbituric acid, triazine compounds, copper compounds, tin compounds, vanadium compounds, halogen compounds, aldehydes, thiol compounds, sulfites, bisulfites, and thiourea compounds. The polymerization accelerator (g) may be used alone, or two or more thereof may be used in combination.

The amines can be divided into aliphatic amines and aromatic amines. Examples of the aliphatic amines include primary aliphatic amines such as n-butylamine, n-hexylamine, and n-octylamine; secondary aliphatic amine such as diisopropylamine, dibutylamine, and N-methylethanolamine; and tertiary aliphatic amines such as N-methyldiethanolamine, N-ethyldiethanolamine, N-n-butyldiethanolamine, N-lauryldiethanolanmine, 2-(dimethylamino)ethylmethacrylate, N-methyldiethanolaminedimethacrylate, N-ethyldiethanolaminedimethacrylate, triethanolaminemonomethacrylate, triethanolaminedimethacrylate, triethanolaminetrimethacrylate, triethanolamine, trimethylamine, triethylamine, and tributylamine. In view of the curability and storage stability of the dental composition, preferred are tertiary aliphatic amines, more preferably N-methyldiethanolamine and triethanolamine.

Examples of the aromatic amines include N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, ethyl 4-(N,N-dimethylamino)benzoate, methyl 4-(N,N-dimethylamino)benzoate, propyl 4-(N,N-dimethylamino)benzoate, n-butoxyethyl 4-(N,N-dimethylamino)benzoate, 2-[(meth)acryloyloxy]ethyl 4-(N,N-dimethylamino)benzoate, 4-(N,N-dimethylamino)benzophenone, and butyl 4-(N,N-dimethylamino)benzoate. In view of imparting desirable cuirability to the composition, preferred is at least one selected from the group consisting of N,N-bis(2-hydroxyethyl)-p-toluidine, ethyl 4-(N,N-dimethylamino)benzoate, n-butoxyethyl 4-(N,N-dimethylamino)benzoate, and 4-(N,N-dimethylamino)benzophenone.

Examples of the sulfinic acid and salts thereof include p-toluenesulfinic acid, sodium p-toluenesulfinate, potassium p-toluenesulfinate, lithium p-toluenesufinate, calcium p-toluenesulfinate, benzenesulfinic acid, sodium benzenesulfinate, potassium benzenesulfinate, lithium benzenesufinate, calcium benzenesulfinate, 2,4,6-trimethylbenzenesulfinic acid, sodium 2,4,6-trimethylbenzenesufinate, potassium 2,4,6-trimethylbenzenesufinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesuinate, calcium 2,4,6-triethylbenzenesulfnate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfnate, and calcium 2,4,6-triisopropylbenzenesulfinate. Particularly preferred are sodium benzenesulfinate, sodium p-toluenesulfinate, and sodium 2,4,6-triisopropylbenzenesulfnate.

Preferred as the borate compounds are arylborate compounds. Examples of arylborate compounds preferred for use include borate compounds having one aryl group per molecule. Specific examples of such borate compounds include trialkylphenylboron, trialkyl(p-chlorophenyl)boron, trialkyl(p-fluorophenyl)boron, trialkyl[3,5-bis(trifluoromethyl)phenyl]boron, trialkyl[3,5-bis(1,1,1,3,3,3-hexafluoro-2-methoxy-2-propyl)phenyl]boron, trialkyl(p-nitrophenyl)boron, trialkyl(m-nitrophenyl)boron, trialkyl(p-butylphenyl)boron, trialkyl(m-butylphenyl)boron, trialkyl(p-butyloxyphenyl)boron, trialkyl(m-butyloxyphenyl)boron, trialkyl(p-octyloxyphenyl)boron, trialkyl(m-octyloxyphenyl)boron (the alkyl group is at least one selected from, for example, the group consisting of an n-butyl group, an n-octyl group, and an n-dodecyl group), and sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts thereof.

Examples of borate compounds having two aryl groups per molecule include dialkyl diphenylboron, dialkyl di(p-chlorophenyl)boron, dialkyl di(p-fluorophenyl)boron, dialkyl di[3,5-bis(trifluoromethyl)phenyl]boron, dialkyl di[3,5-bis(1,1,1,3,3,3-hexafluoro-2-methoxy-2-propyl)phenyl]boron, dialkyl di(p-nitrophenyl)boron, dialkyl di(m-nitrophenyl)boron, dialkyl di(p-butylphenyl)boron, dialkyl di(m-butylphenyl)boron, dialkyl di(p-butyloxyphenyl)boron, dialkyl di(m-butyloxyphenyl)boron, dialkyl di(p-octyloxyphenyl)boron, dialkyl di(m-octyloxyphenyl)boron (the alkyl group is at least one selected from, for example, the group consisting of an n-butyl group, an n-octyl group, and an n-dodecyl group), and sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts thereof.

Examples of borate compounds having three aryl groups per molecule include monoalkyl triphenylboron, monoalkyl tri(p-chlorophenyl)boron, monoalkyl tri(p-fluorophenyl)boron, monoalkyl tri[3,5-bis(trifluoromethyl)phenyl]boron, monoalkyl tri[3,5-bis(1,1,1,3,3,3-hexafluoro-2-methoxy-2-propyl)phenyl]boron, monoalkyl tri(p-nitrophenyl)boron, monoalkyl tri(m-nitrophenyl)boron, monoalkyl tri(p-butylphenyl)boron, monoalkyl tri(m-butylphenyl)boron, monoalkyl tri(p-butyloxyphenyl)boron, monoalkyl tri(m-butyloxyphenyl)boron, monoalkyl tri(p-octyloxyphenyl)boron, monoalkyl tri(m-octyloxyphenyl)boron (the alkyl group is, for example, a group selected from an n-butyl group, an n-octyl group, and an n-dodecyl group), and sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts thereof.

Examples of borate compounds having four aryl groups per molecule include tetraphenylboron, tetrakis(p-chlorophenyl)boron, tetrakis(p-fluorophenyl)boron, tetrakis[3,5-bis(trifluoromethyl)phenyl]boron, tetrakis[3,5-bis(1,1,1,3,3,3-hexafluoro-2-methoxy-2-propyl)phenyl]boron, tetrakis(p-nitrophenyl)boron, tetrakis(m-nitrophenyl)boron, tetrakis(p-butylphenyl)boron, tetrakis(m-butylphenyl)boron, tetrakis(p-butyloxyphenyl)boron, tetrakis(m-butyloxyphenyl)boron, tetrakis(p-octyloxyphenyl)boron, tetrakis(m-octyloxyphenyl)boron, (p-fluorophenyl)triphenylboron, [3,5-bis(trifluoromethyl)phenyl]triphenylboron, (p-nitrophenyl)triphenylboron, (m-butyloxyphenyl)triphenylboron, (p-butyloxyphenyl)triphenylboron, (m-octyloxyphenyl)triphenylboron, (p-octyloxyphenyl)triphenylboron, and sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts thereof.

In view of storage stability, preferred as the arylborate compounds are borate compounds having three or four aryl groups per molecule. The arylborate compounds may be used alone, or two or more thereof may be used as a mixture.

Examples of the derivatives of barbituric acid include barbituric acid, 1,3-dimethylbarbituric acid, 1,3-diphenylbarbituric acid, 1,5-dimethylbarbituric acid, 5-butylbarbituric acid, 5-ethylbarbituric acid, 5-isopropylbarbituric acid, 5-cyclohexylbarbituric acid, 1,3,5-trimethylbarbituric acid, 1,3-dimethyl-5-ethylbarbituric acid, 1,3-dimethyl-5-n-butylbarbituric acid, 1,3-dimethyl-5-isobutylbarbituric acid, 1,3-dimethyl-5-cyclopentylbarbituric acid, 1,3-dimethyl-5-cyclohexylbarbituric acid, 1,3-dimethyl-5-phenylbarbituric acid, 1-cyclohexyl-1-ethylbarbituric acid, 1-benzyl-5-phenylbarbituric acid, 5-methylbarbituric acid, 5-propylbarbituric acid, 1,5-diethylbarbituric acid, 1-ethyl-5-methylbarbituric acid, 1-ethyl-5-isobutylbarbituric acid, 1,3-diethyl-5-butylbarbituric acid, 1-cyclohexyl-5-methylbarbituric acid, 1-cyclohexyl-5-ethylbarbituric acid, 1-cyclohexyl-5-octylbarbituric acid, 1-cyclohexyl-5-hexylbarbituric acid, 5-butyl-1-cyclohexylbarbituric acid, 1-benzyl-5-phenylbarbituric acid, thiobarbituric acids, and salts thereof (particularly preferably, alkali metal salts or alkali-earth metal salts). Examples of the salts of barbituric acids include sodium 5-butylbarbiturate, sodium 1,3,5-trimethylbarbiturate, and sodium 1-cyclohexyl-5-ethylbarbiturate.

Particularly preferred examples of the derivatives of barbituric acid include 5-butylbarbituric acid, 1,3,5-trimethylbarbituric acid, 1-cyclohexyl-5-ethylbarbituric acid, 1-benzyl-5-phenylbarbituric acid, and sodium salts of these barbituric acids.

Examples of the triazine compounds include 2,4,6-tris(trichloromethyl)-s-triazine, 2,4,6-tris(tribromomethyl)-s-triazine, 2-methyl-4,6-bis(trichloromethyl)-s-triazine, 2-methyl-4,6-bis(tribromomethyl)-s-triazine, 2-phenyl-4,6-bis(trichloromethyl)-s-triazine, 2-(p-methoxyphenyl)-4,6-bis(trichloromethyl)-s-triazine, 2-(p-methylthiophenyl)-4,6-bis(trichloromethyl)-s-triazine, 2-(p-chlorophenyl)-4,6-bis(trichloromethyl)-s-triazine, 2-(2,4-dichlorophenyl)-4,6-bis(trichloromethyl)-s-triazine, 2-(p-bromophenyl)-4,6-bis(trichloromethyl)-s-triazine, 2-(p-tolyl)-4,6-bis(trichloromethyl)-s-triazine, 2-n-propyl-4,6-bis(trichloromethyl)-s-triazine, 2-(α,α,ß-trichloroethyl)-4,6-bis(trichloromethyl)-s-triazine, 2-styryl-4,6-bis(trichloromethyl)-s-triazine, 2-[2-(p-methoxyphenyl)ethenyl]-4,6-bis(trichloromethyl)-s-triazine, 2-[2-(o-methoxyphenyl)ethenyl]-4,6-bis(trichloromethyl)-s-triazine, 2-[2-(p-butoxyphenyl)ethenyl]-4,6-bis(trichloromethyl)-s-triazine, 2-[2-(3,4-dimethoxyphenyl)ethenyl]-4,6-bis(trichloromethyl)-s-triazine, 2-[2-(3,4,5-trimethoxyphenyl)ethenyl]-4,6-bis(trichloromethyl)-s-triazine, 2-(1-naphthyl)-4,6-bis(trichloromethyl)-s-triazine, 2-(4-biphenylyl)-4,6-bis(trichloromethyl)-s-triazine, 2-[2-{N,N-bis(2-hydroxyethyl)amino}ethoxy]-4,6-bis(trichloromethyl)-s-triazine, 2-[2-{N-hydroxyethyl-N-ethylamino}ethoxy]-4,6-bis(trichloromethyl)-s-triazine, 2-[2-{N-hydroxyethyl-N-methylamino}ethoxy]-4,6-bis(trichloromethyl)-s-triazine, and 2-[2-{N,N-diallylamino}ethoxy]-4,6-bis(trichloromethyl)-s-triazine.

Among the triazine compounds exemplified above, 2,4,6-tris(trichloromethyl)-s-triazine is particularly preferred in view of polymerization activity, and 2-phenyl-4,6-bis(trichloromethyl)-s-triazine, 2-(p-chlorophenyl)-4,6-bis(trichloromethyl)-s-triazine, and 2-(4-biphenylyl)-4,6-bis(trichloromethyl)-s-triazine are particularly preferred in view of storage stability. The triazine compounds may be used alone, or two or more thereof may be used in combination.

Preferred for use as the copper compounds are, for example, copper acetylacetonate, copper(II) acetate, copper oleate, copper(II) chloride, and copper(II) bromide.

Examples of the tin compounds include di-n-butyltin dimaleate, di-n-octyltin dimaleate, di-n-octyltin dilaurate, and di-n-butyltin dilaurate. The tin compounds are particularly preferably di-n-octyltindilaurate and di-n-butyltindilaurate.

The vanadium compounds are preferably vanadium compounds having a valence of IV and/or V. Examples of vanadium compounds having a valence of IV and/or V include the compounds mentioned in JP 2003-96122 A, including, for example, vanadium(IV) oxide, vanadyl(LV) acetylacetonate, vanadyl oxalate, vanadyl sulfate, vanadium (IV) oxobis(1-phenyl-1,3-butanedionate), bis(maltolato) oxovanadium(IV), vanadium(V) oxide, sodium metavanadate, and ammonium metavanadate.

Examples of the halogen compounds include dilauryldimethylammonium chloride, lauryldimethylbenzylammonium chloride, benzyltrimethylammonium chloride, tetramethylammonium chloride, benzyldimethylcetylammonium chloride, and dilauryldimethylammonium bromide.

Examples of the aldehydes include terephthalaldehyde, and derivatives of benzaldehyde. Examples of the derivatives of benzaldehyde include dimethylaminobenzaldehyde, p-methyloxybenzaldehyde, p-ethyloxybenzaldehyde, and p-n-octyloxybenzaldehyde. In view of curability, preferred for use is p-n-octyloxybenzaldehyde.

Examples of the thiol compounds include 3-mercaptopropyltrimethoxysilane, 2-mercaptobenzooxazole, decanethiol, and thiobenzoic acid.

Examples of the sulfites include sodium sulfite, potassium sulfite, calcium sulfite, and ammonium sulfite.

Examples of the bisulfites include sodium bisulfite and potassium bisulfite.

Examples of the thiourea compounds include 1-(2-pyridyl)-2-thiourea, thiourea, methylthiourea, ethylthiourea, N,N'-dimethylthiourea, 4-methyl-2-imidazolinethione, 4,4-dimethyl-2-imidazolinethione, 4-ethyl-2-imidazolinethione, 4,4-diethyl-2-imidazolinethione, N,N'-diethylthiourea, N,N'-di-n-propylthiourea, N,N'-dicyclohexylthiourea, trimethylthiourea, triethylthiourea, tri-n-propylthiourea, tricyclohexylthiourea, tetramethylthiourea, tetraethylthiourea, tetra-n-propylthiourea, tetracyclohexylthiourea, and 2-pyridylthiourea.

In a dental composition of the present invention, the polymerization accelerator (g) may be used alone, or two or more thereof may be used in combination. The content of polymerization accelerator (g) is not particularly limited. However, in view of the curability and other properties of the dental composition produced, the content of polymerization accelerator (g) preferably ranges from 0.005 to 10 parts by mass, more preferably 0.02 to 5 parts by mass relative to total 100 parts by mass of the radical polymerizable monomer(s) (d). With a polymerization accelerator (g) content of more than 10 parts by mass, it may not be possible to obtain a sufficient bond strength when the polymerization initiator (e) is not highly polymerizable.

Preferably, the dental composition of the present invention further comprises a filler (f). A dental composition of the present invention containing a filler (f) can be prepared into dental materials, for example, such as dental cements and dental composite resins.

Filler (f)

The filler (used in the present invention is preferably a filler used in dentistry. Typically, the filler (f) can be broadly divided into organic filler, inorganic filler, and organic-inorganic composite filler. The filler (f) differs from the platinum nanoparticle (a) and the complex (c). Examples of the material of the organic filler include polymethylmethacrylate, polyethylmethacrylate, a methyl methacrylate-ethyl methacrylate copolymer, crosslinked polymethylmethacrylate, crosslinked polyethylmethacrylate, polyamide, polyvinyl chloride, polystyrene, chloroprene rubber, nitrile rubber, an ethylene-vinyl acetate copolymer, a styrene-butadiene copolymer, an acrylonitrile-styrene copolymer, and an acrylonitrile-styrene-butadiene copolymer. These may be used alone, or two or more thereof may be used as a mixture. The shape of the organic filler is not particularly limited, and the filler may have an appropriately selected particle diameter. In view of ease of handling of the dental composition produced and the mechanical strength and other properties of a cured product of the dental composition, the organic filler has an average particle diameter of preferably 0.001 to 50 µm, more preferably 0.001 to 10 µm. The average particle diameters of various fillers used as filler (can be determined by a laser diffraction scattering method or electron microscopy of filler particles. Specifically, as a convenient way of measuring average particle diameter, filler particles are first measured by a laser diffraction scattering method to see whether the particles have an average particle diameter of 0.1 µm or more. The average particle diameter measured by a laser diffraction scattering method can then be determined as the average particle diameter of the fillers when the measured diameter is 0.1 m or more, whereas electron microscopy is used for average particle diameter measurement when the fillers are ultrafine particles of less than 0.1 µm.

Examples of the material of the inorganic filler include quartz, silica, alumina, silica-titania, silica-titania-barium oxide, siica-zirconia, silica-alumina, lanthanum glass, borosilicate glass, soda glass, barium glass, strontium glass, glass-ceramic, aluminosilicate glass, barium boroaluminosilicate glass, strontium boroaluminosiicate glass, fluoroaluminosilicate glass, calcium fluoroaluminosilicate glass, strontium fluoroaluminosilicate glass, barium fluoroaluminosilicate glass, and strontium calcium fluoroaluminosilicate glass. These may be used alone, or two or more thereof may be used in combination. In view of ease of handling of the dental composition produced and the mechanical strength and other properties of a cured product of the dental composition, the inorganic filler has an average particle diameter of preferably 0.1 to 5 µm.

The inorganic filler may be irregular or spherical in shape. In view of improving the mechanical strength of a cured product of the dental composition produced, the inorganic filler is preferably an irregular filler. As used herein, the spherical filler is a filler having an average uniformity of 0.6 or more as calculated for round-shaped particles observed in a unit field of a scanning electron micrograph (hereinafter, "SEM" for short) of the filler by dividing a particle diameter along a direction orthogonal to the maximum diameter by the maximum diameter. The spherical filler has an average particle diameter of preferably 0.1 to 5 µm. An average particle diameter of less than 0.1 µm may result in decrease of the filling rate of the spherical filler in the curable composition, with the result that the mechanical strength of the cured product decreases. An average particle diameter of more than 5 µm may result in decrease of the surface area of the spherical filler, with the result that the cured product obtained lacks high mechanical strength.

In order to adjust the fluidity of the dental composition, the inorganic filler may be used after an optional surface treatment with a known surface treatment agent such as a silane coupling agent. Examples of such surface treatment agents include vinyltrimethoxysilane, vinyltriethoxysilane, vinyltrichlorosilane, vinyltri(ß-methoxyethoxy)silane, γ-methacryloyloxypropyltrimethoxysilane, 11-methacryloyloxyundecyltrimethoxysilane, γ-glycidoxypropyltrimethoxysilane, γ-mercaptopropyltrimethoxysilane, and γ-aminopropyltriethoxysilane.

The organic-inorganic composite filler is a filler prepared by pulverizing a product of polymerization of a paste-like material prepared by adding a monomer compound to the inorganic filler. Examples of the organic-inorganic composite filler include a TMPT filler (a polymerized and pulverized mixture of trimethylolpropanemethacrylate and a silica filler). The shape of the organic-inorganic composite filler is not particularly limited, and the filler may have an appropriately selected particle diameter. In view of ease of handling of the curable composition obtained and the mechanical strength and other properties of a cured product of the curable composition, the organic-inorganic composite filler has an average particle diameter of preferably 0.001 to 50 m, more preferably 0.001 to 10 μm.

In order to impart fluorine releasability to the dental composition, the filler W used is preferably at least one selected from the group consisting of fluoroaluminosilicate glass, calcium fluoroaluminosilicate glass, strontium fluoroaluminosilicate glass, barium fluoroaluminosilicate glass, and strontium calcium fluoroaluminosilicate glass, more preferably fluoroaluminosilicate glass and/or barium fluoroaluminosilicate glass. In order to impart radiopacity to the dental composition, the filler W used is preferably at least one selected from the group consisting of barium glass, strontium glass, barium boroaluminosilicate glass, strontium boroaluminosilicate glass, strontium fluoroaluminosilicate glass, and barium fluoroaluminosilicate glass, more preferably barium glass and/or barium fluoroaluminosilicate glass.

The content of the filler W in the dental composition is preferably 0.5 to 85 mass %. With a filler (content of less than 0.5 mass %, it may not be possible to obtain the effects of mixing the filler (f), that is, viscosity adjustment of the dental composition, and improvement of the mechanical strength of a cured product of the dental composition. A filler (content of more than 85 mass % may result in overly increasing the viscosity of the dental composition, with the result that ease of procedure deteriorates. A dental composition of the present invention is preferred for use in applications, for example, such as dental bonding agents, dental composite resins, and dental cements, as will be described later. In view of the viscosity of the dental composition, and the mechanical strength of a cured product of the dental composition, the content of the filler W in the dental composition used as a dental composite resin or a dental cement is more preferably 45 to 85 mass %, even more preferably 47 to 80 mass %.

A dental composition of the present invention may contain additional components, for example, such as a fluorine-ion releasing substance, a pH adjuster, a polymerization inhibitor, an ultraviolet absorber, a thickener, a colorant, an antibacterial agent other than the platinum nanoparticle (a), and a flavor, provided that these do not interfere with the effects of the present invention.

A dental composition of the present invention may be a one-component dental composition or a two-component dental composition, as may be appropriately selected for different needs. An embodiment as a two-component dental composition may be a two-part or two-paste dental composition in which the platinum nanoparticle (a), or the complex (c) containing the platinum nanoparticle (a) supported on the surface of the core particle (b) is contained in one of the solutions or one of the pastes. Alternatively, the platinum nanoparticle (a), or the complex (c) containing the platinum nanoparticle (a) supported on the surface of the core particle (b) may be contained in both solutions or both pastes. In a certain embodiment as a dental composition containing a redox polymerization initiator, a first component may contain an oxidizing agent for the redox polymerization initiator (for example, an organic peroxide for the chemical polymerization initiator), and a second component may contain a reducing agent for the redox polymerization initiator (for example, a polymerization accelerator (g) such as a vanadium compound, a copper compound, or a thiourea compound). In the case of a dual cure-type intended for chemical polymerization and photopolymerization, the dental composition of the foregoing embodiment may be a dental component in which the first component additionally contains a polymerization accelerator (g) (for example, an amine) for photopolymerization initiator, and the second component additionally contains a photopolymerization initiator.

The present invention encompasses combinations of the foregoing features, provided that such combinations made in various forms within the technical idea of the present invention can produce the effects of the present invention.

EXAMPLES

The following describes the present invention in greater detail by way of Examples. It should be noted that the present invention is in no way limited by the following Examples. In the Examples, the following abbreviations are used.

Platinum Nanoparticle (a)

The following materials were used as platinum nanoparticle (a). All materials correspond to the complex (c) in which a platinum nanoparticle (a) uncoated with a colloidal protective material is supported on the surface of a core particle (b).

PN-100: a nanoplatinum aqueous solution manufactured by Everywhere Co., Ltd., (nanoplatinum: 10 ppm, core particle: silica, average particle diameter: 500 nm)

PN-1000: a nanoplatinum aqueous solution manufactured by Everywhere Co., Ltd. (nanoplatinum: 100 ppm, core particle: silica, average particle diameter: 500 nm)

PNK-100: a nanoplatinum-catechin aqueous solution manufactured by Everywhere Co., Ltd. (nanoplatinum: 10 ppm, catechin: 100 ppm, core particle: silica and catechin, average particle diameter: 500 nm)

PNK-1000: a nanoplatinum-catechin aqueous solution manufactured by Everywhere Co., Ltd. (nanoplatinum: 100 ppm, catechin: 100 ppm, core particle: silica and catechin, average particle diameter: 500 nm)

PN-100SP: a nanoplatinum ceramic manufactured by Everywhere Co., Ltd. (nanoplatinum: 10 ppm, core particle: silica, average particle diameter: 500 nm)

PN-K050SP: a nanoplatinum-catechin ceramic manufactured by Everywhere Co., Ltd. (nanoplatinum 5 ppm, catechin: 100 ppm, core particle: silica and catechin, average particle diameter: 500 nm)

Radical Polymerizable Monomer (d)
Bis-GMA: 2,2-Bis[4-(3-methacryloyloxy-2-hydroxypropoxy)phenyl]propane
D2.6E: 2,2-Bis(4-(meth)acryloyloxypolyethoxyphenyl)propane (a compound with the average number of moles of ethoxy group added of 2.6)
3G: Triethylene glycol dimethacrylate
801: 1,2-Bis(3-methacryloyloxy-2-hydroxypropoxy)ethane
MDP: 10-Methacryloyloxydecyl dihydrogen phosphate
MAEA: N-Methacryloyloxyethylacrylamide
DEAA: N,N-Diethylacrylamide
TAC4: N,N',N'',N'''-Tetraacryloyltriethylenetetramine Polymerization Initiator (e)
THP: 1,1,3,3-Zetramethylbutylhydroperoxide
CHP: Cumenehydroperoxide
CQ: dl-Camphorquinone Filler (f)
8235: A silane-treated barium glass powder manufactured by Schott; average particle diameter: 2 μm, irregular particle
G018-117: A silane-treated barium fluoroaluminosilicate glass powder manufactured by Schott; average particle diameter: 2 μm, irregular particle
Ar380: AEROSIL® 380, a fine silica particle manufactured by Nippon Aerosil Co., Ltd.; average particle diameter: 7 nm
TAO-CW: A surface-treated fine alumina powder; average particle diameter: 20 nm The surface-treated fine alumina powder was obtained by surface treatment of a fine alumina powder (AEROXIDE® AluC, manufactured by Nippon Aerosil Co., Ltd.) with a 9 mass % organic phosphate compound (10-methacryloyloxydecyl dihydrogen phosphate) and a 9 mass % surface treatment agent (11-methacryloyloxyundecyltrimethoxysilane).

Polymerization Accelerator (g)
VOAA: Vanadyl(IV) acetylacetonate
$Cu(OAc)_2$: Copper(II) acetate
DMETU: 4,4-Dimethyl-2-imidazolinethione
PTU: 2-Pyridylthiourea
JJA: 4-(N,N-Dimethylamino)ethyl benzoate Others
BHT: 3,5-Di-t-butyl-4-hydroxytoluene
TN326: Tinuvin 326 (manufactured by Ciba Specialty Chemicals Inc.)
LBL: Diethyl 2,5-hydroxyterephthalate Antibacterial Materials Containing no Platinum Nanoparticle (a)
MDPB: 12-Methacryloyloxydodecylpyridinium bromide
Nanopure TX-EB14H: A nano-silver dispersion (ethanol) manufactured by Japan Ion Co.
Novaron® AG300: A silver-supporting zirconium phosphate manufactured by Toagosei Co., Ltd.

Production Examples 1 to 11

The components were mixed at ordinary temperature in the compositions shown in Table 1 to prepare monomer compositions (AM01 to AM11) to be used for paste A described below.

Production Examples 12 to 19

The components were mixed at ordinary temperature in the compositions shown in Table 2 to prepare monomer compositions (BM01 to BM08) to be used for paste B described below.

TABLE 1

| | | | Production Example 1 | Production Example 2 | Production Example 3 | Production Example 4 | Production Example 5 | Production Example 6 | Production Example 7 | Production Example 8 | Production Example 9 | Production Example 10 | Production Example 11 |
|---|---|---|---|---|---|---|---|---|---|---|---|---|---|
| | Monomer composition A | | AM01 | AM02 | AM03 | AM04 | AM05 | AM06 | AM07 | AM08 | AM09 | AM10 | AM11 |
| (Parts by mass) | Complex (c) in which platinum nanoparticle (a) is supported on surface of core particle (b) | PN-100 | 10.0 | | | | | | | | | | |
| | | PN-1000 | | 2.00 | | | | | | | | | |
| | | PNK-100 | | | 10.0 | | | | | | | | |
| | | PNK-1000 | | | | 2.00 | | | | | | | |
| | Antibacterial material containing no platinum nanoparticle (a) | MDPB | | | | | | | | | | | 5.00 |
| | (Meth)acrylate polymerizable monomer (d1) | Bis-GMA | 31.0 | 35.0 | 31.0 | 35.0 | 36.0 | 36.0 | 36.0 | 36.0 | 36.0 | 36.0 | 36.0 |
| | | D2.6E | 32.0 | 36.0 | 32.0 | 36.0 | 37.0 | 37.0 | 37.0 | 37.0 | 37.0 | 37.0 | 37.0 |
| | | 3G | 17.0 | 17.0 | 17.0 | 17.0 | 17.0 | 12.0 | 7.0 | 5.0 | 5.0 | 17.0 | 17.0 |
| | | #801 | 10.0 | 10.0 | 10.0 | 10.0 | 10.0 | 10.0 | 10.0 | 10.0 | 10.0 | 10.0 | 10.0 |
| | (Meth)acrylamide polymerizable monomer (d2) | MAEA | | | | | | | | | 10.0 | 10.0 | |
| | | TAC4 | | | | | | | | 2.00 | | | |
| | | DEAA | | | | | | | | | | 2.00 | |
| | Acidic group-containing radical polymerizable monomer (d3) | MDP | | | | | | 5.00 | 10.00 | | | | |

TABLE 1-continued

|  |  | Production Example 1 | Production Example 2 | Production Example 3 | Production Example 4 | Production Example 5 | Production Example 6 | Production Example 7 | Production Example 8 | Production Example 9 | Production Example 10 | Production Example 11 |
|---|---|---|---|---|---|---|---|---|---|---|---|---|
| Polymerization initiator (e) | THP | 4.00 | 4.00 | 4.00 | 4.00 | 4.00 | 4.00 | 4.00 | 4.00 | 4.00 |  | 4.00 |
|  | CHP |  |  |  |  |  |  |  |  |  | 4.00 |  |
| Polymerization accelerator (g) | JJA | 0.250 | 0.250 | 0.250 | 0.250 | 0.250 | 0.250 | 0.250 | 0.250 | 0.250 | 0.250 | 0.250 |
| Other | BHT | 0.0700 | 0.0700 | 0.0700 | 0.0700 | 0.0700 | 0.0700 | 0.0700 | 0.0700 | 0.0700 | 0.0700 | 0.0700 |
|  | TN326 | 0.225 | 0.225 | 0.225 | 0.225 | 0.225 | 0.225 | 0.225 | 0.225 | 0.225 | 0.225 | 0.225 |
|  | LBL | 0.0800 | 0.0800 | 0.0800 | 0.0800 | 0.0800 | 0.0800 | 0.0800 | 0.0800 | 0.080 | 0.0800 | 0.0800 |

TABLE 2

|  |  |  | Production Example 12 | Production Example 13 | Production Example 14 | Production Example 15 | Production Example 16 | Production Example 17 | Production Example 18 | Production Example 19 |
|---|---|---|---|---|---|---|---|---|---|---|
|  | Monomer composition B |  | BM01 | BM02 | BM03 | BM04 | BM05 | BM06 | BM07 | BM08 |
| (Parts by mass) | Complex (c) in which platinum nanoparticle (a) is supported on surface of core particle (b) | PN-100 |  | 10.0 |  |  |  |  |  |  |
|  |  | PN-1000 |  |  | 2.00 |  |  |  |  |  |
|  |  | PNK-100 |  |  |  | 10.0 |  |  |  |  |
|  |  | PNK-1000 |  |  |  |  | 2.00 |  |  |  |
|  | Antibacterial material containing no platinum nanoparticle (a) | MDPB |  |  |  |  |  |  |  | 5.00 |
|  | (Meth)acrylate polymerizable monomer (d1) | Bis-GMA | 15.0 | 15.0 | 15.0 | 15.0 | 15.0 | 15.0 | 15.0 | 15.0 |
|  |  | D2.6E | 70.0 | 70.0 | 70.0 | 70.0 | 70.0 | 70.0 | 70.0 | 70.0 |
|  |  | #801 | 15.0 | 15.0 | 15.0 | 15.0 | 15.0 | 15.0 | 15.0 | 15.0 |
|  | Polymerization initiator (e) | CQ | 0.200 | 0.200 | 0.200 | 0.200 | 0.200 | 0.200 | 0.200 | 0.200 |
|  | Polymerization accelerator (g) | VOAA | 0.100 | 0.100 | 0.100 | 0.100 | 0.100 |  | 0.100 | 0.100 |
|  |  | Cu(OAc)$_2$ |  |  |  |  |  | 0.0100 |  |  |
|  |  | DMETU | 5.00 | 5.00 | 5.00 | 5.00 | 5.00 | 5.00 |  | 5.00 |
|  |  | PTU |  |  |  |  |  |  | 2.00 |  |
|  | Other | BHT | 0.150 | 0.150 | 0.150 | 0.150 | 0.150 | 0.150 | 0.150 | 0.150 |

Examples 1 to 23 and Comparative Examples 1 to 6

Dental compositions of Examples 1 to 23 and Comparative Examples 1 to 6 were prepared as follows.

Preparation of Dental Composition

The monomer compositions (monomer composition A, monomer composition B) and fillers were mixed at ordinary temperatures in the compositions shown in Tables 3 to 5 to prepare paste A and paste B. In Examples 5 to 13, complex (c) was added to paste A in the amounts shown in Table 3, in addition to the monomer composition and the filler. In Examples 18 to 23, complex (c) was added to paste B in the amounts shown in Table 4. The paste (paste B only, 15 g each) was transferred to a resin container for Clearfil® FII (manufactured by Kuraray Noritake Dental Inc.), and, after placing the cap, the container was allowed to stand in a 60° C. thermostatic chamber for 24 hours, and brought back to 25° C. Separately, the paste A and paste B were then charged into a paste container for automix syringe Panavia® V5 (manufactured by Kuraray Noritake Dental Inc.). In obtaining a dental composition by mixing paste A and paste B, paste A and paste B were mixed in equal amounts in a volume ratio of 1:1 using a mixing tip (Panavia® V5 mixing tip (for luting), manufactured by Kuraray Noritake Dental Inc.) attached to the tip of the paste container.

Comparative Example 7

In Comparative Example 7, Block HC Sem (an ion releasing filler (S-PRG filler) formulation, manufactured by Shofu Inc.) was used as a dental composition.

The dental compositions of Examples and Comparative Examples were evaluated using the following methods. The evaluation results are presented in Tables 3 to 5.

Measurement of Antibacterial Activity Value Immediately after Fabrication of Cured Product of Cured Paste A Teflon® mold was placed on glass, and another glass plate was placed over a dental composition prepared by the foregoing method and mounted in the mold. After pressing the glass plates against each other, the dental composition was exposed to light for 2 minutes each side with an α Light III (manufactured by J. Morita Corp.) to completely cure the paste. The resulting sample of cured paste (measuring 5 cm in length, 5 cm in width, and 1 mm in thickness) was ground with a lapping film sheet (manufactured by 3M Company, grain size: 1 micron) to expose a flat surface. The sample was then tested for antibacterial activity against *Streptococcus mutans* (*Streptococcus mutans* IFO 13955) according to the method described in JIS Z 2801:2012, and an antibacterial activity value was calculated. The antibacterial activity value is an index of antibacterial activity. The preferred antibacterial activity value is 2.0 or more.

Measurement of Antibacterial Activity Value of Cured Paste after Immersion in 37° C. Water for One Month A cured paste sample (measuring 5 cm in length, 5 cm in width, and 1 mm in thickness) fabricated from the dental composition was ground with a lapping film sheet (manufactured by 3M Company, grain size: 1 micron) to expose a flat surface, as in the measurement of antibacterial activity value immediately after fabrication of a cured product. The sample was transferred into a screw cap tube, and, after injecting distilled water, allowed to stand in a 37° C. thermostatic chamber for 1 month with the cap tightly screwed. The sample was then tested for antibacterial activity against *Streptococcus mutans* (*Streptococcus mutans* IFO 13955) according to the method described in JIS Z 2801: 2012, and an antibacterial activity value was calculated. The antibacterial activity value is an index of antibacterial activity. The preferred antibacterial activity value is 2.0 or more.

Measurement of Transparency Change in Cured Paste in Water

The dental composition prepared using the foregoing method was fabricated into a disc-shaped sample (measuring about 2 cm in diameter, and 1 mm in thickness). First, a cover glass was placed on a glass slide, and a pair of plate-shaped stainless-steel spacers (each having a thickness of 1 mm) was mounted side by side, at least 2.5 cm apart. The dental composition prepared using the foregoing method was then placed between the two spacers in a hemispherical shape, and another cover glass with a glass slide was placed over the dental composition. The dental composition placed between the glass slides was pressed into a disc shape, and was allowed to stand in a 37° C. thermostatic chamber in this state for 1 hour to completely cure the paste. Because the test result greatly fluctuates with sample thickness, the sample thickness was confined within a range of 0.99 to 1.00 mm (with the thickest portion as thick as 1.00 mm, and the thinnest portion as thin as 0.99 mm).

In the test, the cured paste was measured for luminance (Lw*)—a chromaticity measured against a standard white plate placed behind the specimen, and luminance (Lb*)—a chromaticity measured against a standard black plate placed behind the specimen, and the difference between these values ($\Delta L^* = (Lw^*) - (Lb^*)$) was calculated as the transparency ($\Delta L^*0$) of the cured paste. The test was conducted with a spectrophotometer (manufactured by Nippon Denshoku Industries Co., Ltd.; trade name SE 6000) satisfying the conditions described in JIS Z 8781-4:2013, using a D65 illuminant with a viewing angle of 2 degrees. The sample was then transferred into a screw cap tube, and, after injecting distilled water, allowed to stand in a 70° C. thermostatic chamber for 4 weeks with the cap tightly screwed. The stored sample of cured product was also measured for transparency ($\Delta L^*$), denoted as $\Delta L^*1$, using the same technique. The measured values were substituted in the following formula to determine $\Delta\Delta L^*$, an index of transparency change.

$$\Delta\Delta L^* = \Delta L^*1 - \Delta L^*0$$

Measurement of Discoloration of Cured Paste in Water

A disc-shaped sample (measuring about 2 cm in diameter and 1 mm in thickness) of the cured paste fabricated from the dental composition was measured for L*a*b* chromaticity against a standard white plate placed behind the specimen. The test was conducted with a spectrophotometer (manufactured by Nippon Denshoku Industries Co., Ltd.; trade name SE 6000) satisfying the conditions described in JIS Z 8781-4:2013, using a D65 illuminant with a viewing angle of 2 degrees, as in the measurement of transparency change in water described above. The measured values were denoted as L*0, a*0, and b*0. The sample was then transferred into a screw cap tube, and, after injecting distilled water, allowed to stand in a 70° C. thermostatic chamber for 4 weeks with the cap tightly screwed. The stored sample was also measured for L*a*b* chromaticity using the same technique. The measured values were denoted as L*1, a*1, and b*1. The measured values were substituted in the following formula to determine $\Delta E^*$, an index of discoloration.

$$\Delta E^* = \{(L^*1 - L^*0)^2 + (a^*1 - a^*0)^2 + (b^*1 - b^*0)^2\}^{1/2}$$

Measurement of Discoloration of Cured Paste after Exposure to Hydrogen Sulfide A disc-shaped sample (measuring about 2 cm in diameter and 1 mm in thickness) of the cured paste fabricated from the dental composition was measured for L*a*b* chromaticity against a standard white plate placed behind the specimen. The test was conducted with a spectrophotometer (manufactured by Nippon Denshoku Industries Co., Ltd.; trade name SE 6000) satisfying the conditions described in JIS Z 8781-4:2013, using a D65 illuminant with a viewing angle of 2 degrees, as in the measurement of transparency change in water described above. The measured values were denoted as L*0, a*0, and b*0. The sample was then transferred into a screw cap tube. After injecting a 10 mass % sodium sulfide aqueous solution (2.7 g, 3.5 mmol) and 3 mass % hydrochloric acid (8.1 g, 6.7 mmol) in this order, the sample was allowed to stand in a 60° C. thermostatic chamber for 10 hours with the cap loosely screwed. The stored sample was also measured for L*a*b* chromaticity using the same technique. The measured values were denoted as L*1, a*1, and b*1. The measured values were substituted in the following formula to determine $\Delta E^*$, an index of discoloration.

$$\Delta E^* = \{(L^*1 - L^*0)^2 + (a^*1 - a^*0)^2 + (b^*1 - b^*0)^2\}^{1/2}$$

TABLE 3

|  |  |  | Example 1 | Example 2 | Example 3 | Example 4 | Example 5 | Example 6 | Example 7 |
|---|---|---|---|---|---|---|---|---|---|
|  | Paste A |  | AP01 | AP02 | AP03 | AP04 | AP05 | AP06 | AP07 |
| (Parts | Monomer composition A | AM01 | 38.0 |  |  |  |  |  |  |
| by |  | AM02 |  | 38.0 |  |  |  |  |  |
| mass) |  | AM03 |  |  | 38.0 |  |  |  |  |
|  |  | AM04 |  |  |  | 38.0 |  |  |  |
|  |  | AM05 |  |  |  |  | 38.0 | 38.0 | 38.0 |
|  |  | AM06 |  |  |  |  |  |  |  |
|  |  | AM07 |  |  |  |  |  |  |  |
|  |  | AM08 |  |  |  |  |  |  |  |
|  |  | AM09 |  |  |  |  |  |  |  |
|  |  | AM10 |  |  |  |  |  |  |  |

TABLE 3-continued

|  |  |  |  |  |  |  |  |  |  |
|---|---|---|---|---|---|---|---|---|---|
| Complex (c) in which platinum nanoparticle (a) is supported on surface of core particle (b) | PN-100SP |  |  |  |  | 10.0 | 20.0 |  |
|  | PN-K050SP |  |  |  |  |  |  | 10.0 |
| Filler (f) | 8235 | 51.0 | 51.0 | 51.0 | 51.0 | 42.0 | 32.0 | 42.0 |
|  | G018-117 | 10.0 | 10.0 | 10.0 | 10.0 | 10.0 | 10.0 | 10.0 |
|  | Ar380 | 1.00 | 1.00 | 1.00 | 1.00 |  |  |  |
| Paste B |  | BP01 | BP01 | BP01 | BP01 | BP01 | BP01 | BP01 |
| (Parts by mass) Monomer composition B | BM01 | 40.0 | 40.0 | 40.0 | 40.0 | 40.0 | 40.0 | 40.0 |
| Filler (f) | 8235 | 54.0 | 54.0 | 54.0 | 54.0 | 54.0 | 54.0 | 54.0 |
|  | TAO-CW | 6.00 | 6.00 | 6.00 | 6.00 | 6.00 | 6.00 | 6.00 |
| Content of platinum nanoparticle (a) relative to total dental composition (ppm by mass) |  | 0.19 | 0.38 | 0.19 | 0.38 | 0.50 | 1.00 | 0.25 |
| Antibacterial activity value immediately after fabrication of cured product |  | 2.2 | 2.1 | 2.2 | 2.3 | 2.1 | 2.1 | 2.3 |
| Antibacterial activity value after immersion in 37° C. water for 1 month |  | 2.0 | 2.0 | 2.1 | 2.1 | 2.0 | 2.0 | 2.1 |
| Transparency change after immersion in 70° C. water for 4 weeks $\Delta\Delta L^*$ |  | −4.8 | −4.9 | −5.0 | −5.0 | −4.5 | −4.9 | −3.9 |
| Color change after immersion in 70° C. water for 4 weeks $\Delta E^*$ |  | 2.1 | 2.9 | 2.6 | 2.9 | 1.8 | 2.1 | 2.6 |
| Color change after 10-hour exposure to 60° C. hydrogen sulfide $\Delta E^*$ |  | 4.3 | 4.9 | 4.3 | 4.9 | 4.0 | 4.5 | 4.1 |

|  |  | Example 8 | Example 9 | Example 10 | Example 11 | Example 12 | Example 13 |
|---|---|---|---|---|---|---|---|
| Paste A |  | AP08 | AP09 | AP10 | AP11 | AP12 | AP13 |
| (Parts by mass) Monomer composition A | AM01 |  |  |  |  |  |  |
|  | AM02 |  |  |  |  |  |  |
|  | AM03 |  |  |  |  |  |  |
|  | AM04 |  |  |  |  |  |  |
|  | AM05 | 38.0 |  |  |  |  |  |
|  | AM06 |  | 38.0 |  |  |  |  |
|  | AM07 |  |  | 38.0 |  |  |  |
|  | AM08 |  |  |  | 38.0 |  |  |
|  | AM09 |  |  |  |  | 38.0 |  |
|  | AM10 |  |  |  |  |  | 38.0 |
| Complex (c) in which platinum nanoparticle (a) is supported on surface of core particle (b) | PN-100SP |  |  |  |  |  |  |
|  | PN-K050SP | 20.0 | 10.0 | 10.0 | 10.0 | 10.0 | 10.0 |
| Filler (f) | 8235 | 32.0 | 42.0 | 42.0 | 42.0 | 42.0 | 42.0 |
|  | G018-117 | 10.0 | 10.0 | 10.0 | 10.0 | 10.0 | 10.0 |
|  | Ar380 |  |  |  | 1.00 | 0.00 | 0.00 |
| Paste B |  | BP01 | BP01 | BP01 | BP01 | BP01 | BP01 |
| (Parts by mass) Monomer composition B | BM01 | 40.0 | 40.0 | 40.0 | 40.0 | 40.0 | 40.0 |
| Filler (f) | 8235 | 54.0 | 54.0 | 54.0 | 54.0 | 54.0 | 54.0 |
|  | TAO-CW | 6.00 | 6.00 | 6.00 | 6.00 | 6.00 | 6.00 |
| Content of platinum nanoparticle (a) relative to total dental composition (ppm by mass) |  | 0.50 | 0.25 | 0.25 | 0.25 | 0.25 | 0.25 |
| Antibacterial activity value immediately after fabrication of cured product |  | 2.3 | 2.3 | 2.2 | 2.2 | 2.3 | 2.2 |
| Antibacterial activity value after immersion in 37° C. water for 1 month |  | 2.1 | 2.1 | 2.0 | 2.0 | 2.1 | 2.0 |
| Transparency change after immersion in 70° C. water for 4 weeks $\Delta\Delta L^*$ |  | −4.6 | −5.0 | −5.0 | −3.9 | −3.2 | −3.6 |
| Color change after immersion in 70° C. water for 4 weeks $\Delta E^*$ |  | 2.8 | 2.9 | 2.9 | 2.4 | 2.1 | 2.2 |
| Color change after 10-hour exposure to 60° C. hydrogen sulfide $\Delta E^*$ |  | 4.7 | 4.9 | 4.8 | 4.1 | 4.0 | 3.9 |

TABLE 4

|  |  | Example 14 | Example 15 | Example 16 | Example 17 | Example 18 | Example 19 |
|---|---|---|---|---|---|---|---|
| Paste A |  | AP14 | AP14 | AP14 | AP14 | AP14 | AP14 |
| (Parts by mass) Monomer composition A | AM05 | 38.0 | 38.0 | 38.0 | 38.0 | 38.0 | 38.0 |
| Filler (f) | 8235 | 51.0 | 51.0 | 51.0 | 51.0 | 51.0 | 51.0 |
|  | G018-117 | 10.0 | 10.0 | 10.0 | 10.0 | 10.0 | 10.0 |
|  | Ar380 | 1.00 | 1.00 | 1.00 | 1.00 | 1.00 | 1.00 |
| Paste B |  | BP02 | BP03 | BP04 | BP05 | BP06 | BP07 |
| (Parts by mass) Monomer composition B | BM01 |  |  |  |  | 40.0 | 40.0 |
|  | BM02 | 40.0 |  |  |  |  |  |
|  | BM03 |  | 40.0 |  |  |  |  |
|  | BM04 |  |  | 40.0 |  |  |  |
|  | BM05 |  |  |  | 40.0 |  |  |
|  | BM06 |  |  |  |  |  |  |
|  | BM07 |  |  |  |  |  |  |
| Complex (c) in which platinum nanoparticle (a) is supported on surface of core particle (b) | PN-100SP |  |  |  |  | 10.0 | 20.0 |
|  | PN-K050SP |  |  |  |  |  |  |
| Filler (f) | 8235 | 54.0 | 54.0 | 54.0 | 54.0 | 44.0 | 3.40 |
|  | TAO-CW | 6.00 | 6.00 | 6.00 | 6.00 | 6.00 | 6.00 |
| Content of platinum nanoparticle (a) relative to total dental composition (ppm by mass) |  | 0.20 | 0.40 | 0.20 | 0.40 | 0.50 | 1.00 |
| Antibacterial activity value immediately after fabrication of cured product |  | 2.3 | 2.2 | 2.2 | 2.2 | 2.2 | 2.2 |
| Antibacterial activity value after immersion in 37° C. water for 1 month |  | 2.1 | 2.0 | 2.0 | 2.1 | 2.1 | 2.1 |
| Transparency change after immersion in 70° C. water for 4 weeks ΔΔL* |  | −4.9 | −4.8 | −3.9 | −3.7 | −5.0 | −5.0 |
| Color change after immersion in 70° C. water for 4 weeks ΔE* |  | 2.0 | 2.4 | 2.1 | 2.9 | 1.6 | 2.3 |
| Color change after 10-hour exposure to 60° C. hydrogen sulfide ΔE* |  | 2.0 | 2.6 | 3.4 | 3.8 | 2.3 | 3.2 |

|  |  | Example 20 | Example 21 | Example 22 | Example 23 |
|---|---|---|---|---|---|
| Paste A |  | AP14 | AP14 | AP14 | AP14 |
| (Parts by mass) Monomer composition A | AM05 | 38.0 | 38.0 | 38.0 | 38.0 |
| Filler (f) | 8235 | 51.0 | 51.0 | 51.0 | 51.0 |
|  | G018-117 | 10.0 | 10.0 | 10.0 | 10.0 |
|  | Ar380 | 1.00 | 1.00 | 1.00 | 1.00 |
| Paste B |  | BP08 | BP09 | BP10 | BP11 |
| (Parts by mass) Monomer composition B | BM01 | 40.0 | 40.0 |  |  |
|  | BM02 |  |  |  |  |
|  | BM03 |  |  |  |  |
|  | BM04 |  |  |  |  |
|  | BM05 |  |  |  |  |
|  | BM06 |  |  | 40.0 |  |
|  | BM07 |  |  |  | 40.0 |
| Complex (c) in which platinum nanoparticle (a) is supported on surface of core particle (b) | PN-100SP |  |  |  |  |
|  | PN-K050SP | 10.0 | 20.0 | 10.0 | 10.0 |
| Filler (f) | 8235 | 44.0 | 34.0 | 44.0 | 44.0 |
|  | TAO-CW | 6.00 | 6.00 | 6.00 | 6.00 |
| Content of platinum nanoparticle (a) relative to total dental composition (ppm by mass) |  | 0.25 | 0.50 | 0.25 | 0.25 |
| Antibacterial activity value immediately after fabrication of cured product |  | 2.5 | 2.5 | 2.5 | 2.5 |
| Antibacterial activity value after immersion in 37° C. water for 1 month |  | 2.3 | 2.3 | 2.3 | 2.3 |
| Transparency change after immersion in 70° C. water for 4 weeks ΔΔL* |  | −3.9 | −4.6 | −4.3 | −4.6 |
| Color change after immersion in 70° C. water for 4 weeks ΔE* |  | 2.1 | 2.6 | 2.3 | 2.4 |
| Color change after 10-hour exposure to 60° C. hydrogen sulfide ΔE* |  | 3.5 | 4.0 | 3.9 | 4.1 |

TABLE 5

|  |  |  | Com. Ex. 1 | Com. Ex. 2 | Com. Ex. 3 | Com. Ex. 4 | Com. Ex. 5 | Com. Ex. 6 | Com Ex. 7 |
|---|---|---|---|---|---|---|---|---|---|
| (Parts by mass) | Paste A Monomer composition A | AM05 AM11 | A015 38.0 | A014 38.0 | A016 38.0 | A014 38.0 | A017 38.0 | A014 38.0 | Block HC Sem |
|  | Antibacterial material containing no platinum nanoparticle (a) | Nanopure TX-EB14H Novaron AG300 |  |  | 10.0 |  | 10.0 |  |  |
|  | Filler (f) | 8235 G018-117 Ar380 | 51.0 10.0 1.00 | 51.0 10.0 1.00 | 41.0 10.0 1.00 | 51.0 10.0 1.00 | 41.0 10.0 1.00 | 51.0 10.0 1.00 |  |
| (Parts by mass) | Paste B Monomer composition B | BM01 BM08 | B001 40.0 | B012 40.0 | B001 40.0 | B015 40.0 | B013 40.0 | B016 40.0 |  |
|  | Antibacterial material containing no platinum nanoparticle (a) | Nanopure TX-EB14H Novaron AG300 |  |  |  | 10.0 |  | 10.0 |  |
|  | Filler (f) | 8235 TAO-CW | 54.0 6.00 | 54.0 6.00 | 54.0 6.00 | 44.0 6.00 | 54.0 6.00 | 44.0 6.00 |  |
| Antibacterial activity value immediately after fabrication of cured product |  |  | 1.8 | 1.7 | 2.5 | 2.5 | 2.5 | 2.5 | 2.3 |
| Antibacterial activity value after immersion in 37° C. water for 1 month |  |  | 1.0 | 1.1 | 2.3 | 2.3 | 2.3 | 2.3 | 1.0 |
| Transparency change after immersion in 70° C. water for 4 weeks ΔΔL* |  |  | −8.9 | −8.7 | −18.9 | −19.2 | −14.3 | −14.3 | −8.6 |
| Color change after immersion in 70° C. water for 4 weeks ΔE* |  |  | 6.8 | 7.1 | 21.2 | 18.9 | 16.8 | 18.9 | 10.7 |
| Color change after 10-hour exposure to 60° C. hydrogen sulfide ΔE* |  |  | 4.8 | 4.9 | 40.1 | 35.7 | 20.5 | 25.9 | 7.4 |

As shown in Tables 3 and 4, the dental compositions of the present invention had desirable antibacterial activity with antibacterial activity values of 2.0 and higher, both immediately after curing and after post-curing immersion in 37° C. water for 1 month. The dental compositions of the present invention also showed desirable aesthetic quality, as demonstrated by the cured products showing a transparency change ΔΔL* of −5.0 to 0.0 after 4 weeks in 70° C. water, a discoloration ΔE* of 3 or less after 4 weeks in 70° C. water, and a discoloration ΔE* of 5 or less after 10-hour exposure to 60° C. hydrogen sulfide. In contrast, as shown in Table 5, Comparative Examples 1, 2, and 7 had antibacterial activity values of 1.1 and lower after post-curing immersion in 37° C. water for 1 month, and did not show antibacterial activity. In Comparative Examples 3 to 5 and 6, the cured products showed antibacterial activity immediately after fabrication and after immersion in 37° C. water for 1 month. However, the cured products had poor aesthetic quality with a transparency change ΔΔL* of −12.0 or less observed after 4 weeks in 70° C. water, and with severe discoloration as exhibited by a discoloration ΔE* of 15.0 or more after 4 weeks in 70° C. water, and a discoloration ΔE* of 20 or more after 10-hour exposure to 60° C. hydrogen sulfide.

INDUSTRIAL APPLICABILITY

A dental composition according to the present invention exhibits excellent long-lasting antibacterial activity even as a cured product, and excels in aesthetic quality with no discoloration occurring in water or in hydrogen sulfide. This makes a dental composition according to the present invention suitable as a dental material, for example, such as a dental bonding agent, a dental cement, or a dental composite resin.

The invention claimed is:

1. A dental composition, comprising a complex (c) in which a platinum nanoparticle (a) is supported on a surface of a core particle (b),
   wherein the platinum nanoparticle (a) is uncoated with a colloidal protective material.

2. The dental composition of claim 1, wherein the core particle (b) comprises at least one selected from the group consisting of a ceramic, catechin, a vitamin derivative, astaxanthin, a placenta extract, a coenzyme, and hyaluronan.

3. The dental composition of claim 1, wherein the dental composition further comprises a radical polymerizable monomer (d) and a polymerization initiator (e).

4. The dental composition of claim 3, wherein the radical polymerizable monomer (d) is at least one selected from the group consisting of a (meth)acrylate polymerizable monomer (d1) and a (meth)acrylamide polymerizable monomer (d2).

5. The dental composition of claim 4, wherein the (meth)acrylate polymerizable monomer (d1) comprises at least one selected from the group consisting of an aromatic bifunctional (meth)acrylate polymerizable monomer and an aliphatic bifunctional (meth)acrylate polymerizable monomer.

6. The dental composition of claim 1, comprising from 0.005 ppm to 5.0 ppm by mass of the platinum nanoparticle (a).

7. The dental composition of claim 1, further comprising a filler (f).

8. The dental composition of claim 1, comprising from 0.05 ppm to 2.5 ppm by mass of the platinum nanoparticle (a).

9. The dental composition of claim 1, wherein the platinum nanoparticle (a) has an average particle diameter of from 1 nm to 50 nm.

10. The dental composition of claim 1, wherein the core particle (b) has an average particle diameter of from 0.01 μm to 10 μm.

11. The dental composition of claim 3, wherein the polymerization initiator (e) is at least one photopolymerization initiator selected from the group consisting of a (bis) acylphosphine oxide, an α-diketone, and a coumarin.

12. The dental composition of claim 3, wherein the polymerization initiator (e) is at least one chemical polymerization initiator selected from the group consisting of a ketone peroxide, hydroperoxide, diacyl peroxide, dialkyl peroxide, peroxy ketal, peroxy ester, and peroxy dicarbonate.

13. The dental composition of claim 3, wherein a content of the polymerization initiator (e) is from 0.005 parts by mass to 10 parts by mass based on 100 parts by mass of the radical polymerizable monomer (d).

14. The dental composition of claim 3, wherein a content of the polymerization initiator (e) is from 0.02 parts by mass to 5 parts by mass based on 100 parts by mass of the radical polymerizable monomer (d).

15. The dental composition of claim 3, further comprising from 0.005 parts by mass to 10 parts by mass of a polymerization accelerator (g) based on 100 parts by mass of the radical polymerizable of monomer (d).

16. The dental composition of claim 3, further comprising from 0.02 parts by mass to 5 parts by mass of a polymerization accelerator (g) based on 100 parts by mass of the radical polymerizable of monomer (d).

17. The dental composition of claim 7, wherein the filler (f) is an organic filler having an average particle diameter of from 0.001 μm to 50 μm.

18. The dental composition of claim 7, wherein the filler (f) is an inorganic filler having an average particle diameter of from 0.1 μm to 5 μm.

19. The dental composition of claim 7, wherein a content of the filler (f) in the dental composition is from 0.5 mass % to 85 mass %.

* * * * *